United States Patent
Janssen et al.

(10) Patent No.: US 6,825,391 B2
(45) Date of Patent: Nov. 30, 2004

(54) REJUVENATING SAPO MOLECULAR SIEVE WITH ANHYDROUS LIQUID OR VAPOR

(75) Inventors: Marcel J. G. Janssen, Kessel-Lo (BE); Cornelius W. M. Van Oorschot, Braschaat (BE); Kenneth R. Clem, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 305 days.

(21) Appl. No.: 10/211,093

(22) Filed: Aug. 2, 2002

(65) Prior Publication Data

US 2003/0028062 A1 Feb. 6, 2003

Related U.S. Application Data

(62) Division of application No. 09/615,526, filed on Jul. 13, 2000, now Pat. No. 6,448,197, and a division of application No. 09/558,774, filed on Apr. 26, 2000, now Pat. No. 6,498,120.

(51) Int. Cl.[7] .................................................. C07C 1/00
(52) U.S. Cl. ......................................................... 585/640
(58) Field of Search ................................. 585/639, 640, 585/654, 661

(56) References Cited

U.S. PATENT DOCUMENTS

| | | | | |
|---|---|---|---|---|
| 4,319,057 A | * | 3/1982 | Kiser | 568/916 |
| 4,681,864 A | * | 7/1987 | Edwards et al. | 502/63 |
| 4,842,714 A | * | 6/1989 | Pellet et al. | 208/114 |
| 5,177,298 A | * | 1/1993 | Yon et al. | 585/824 |
| 5,185,310 A | * | 2/1993 | Degnan et al. | 502/214 |
| 5,248,647 A | * | 9/1993 | Barger | 502/214 |
| 5,744,680 A | * | 4/1998 | Mulvaney et al. | 585/640 |
| 5,912,393 A | * | 6/1999 | Barger et al. | 585/640 |
| 5,932,512 A | * | 8/1999 | Sun | 502/214 |
| 2001/0020119 A1 | * | 9/2001 | Janssen et al. | 585/638 |

FOREIGN PATENT DOCUMENTS

WO    WO 9310065 A1 * 5/1993 ............ B01J/20/34

* cited by examiner

*Primary Examiner*—Stanley S. Silverman
*Assistant Examiner*—Edward M. Johnson (57) ABSTRACT

Disclosed is a method of rejuvenating a molecular sieve. The method includes contacting a molecular sieve having a methanol uptake of less than 1, or a catalyst containing molecular sieve having a methanol up of less than 1, with anhydrous liquid or vapor until the methanol uptake ratio is increased by at least 10%. The rejuvenated molecular sieve or catalyst can be used to make an olefin product from an oxygenate-containing feedstock. The preferred molecular sieve is a silicoaluminophosphate (SAPO) molecular sieve.

22 Claims, 2 Drawing Sheets

REJUVENATING SAPO MOLECULAR SIEVE WITH ANHYDROUS LIQUID OR VAPOR

This is a division of application Ser. No. 09/615,526, filed Jul. 13, 2000, now U.S. Pat. No. 6,448,197, and is a division of application Ser. No. 09/558,774, filed Apr. 26, 2000, now U.S. Pat. No. 6,498,120.

FIELD OF THE INVENTION

This invention is directed to a method of rejuvenating silicoaluminophosphate (SAPO) molecular sieve catalyst, and a method of using the rejuvenated catalyst to make an olefin product from methanol feed. In particular, the invention is directed to rejuvenating the sieve by contacting the molecular sieve with anhydrous, polar liquid or vapor until a desired methanol uptake ratio is achieved.

BACKGROUND OF THE INVENTION

Silicoaluminophosphates (SAPOs) have been used as adsorbents and catalysts. As catalysts, SAPOs have been used in processes such as fluid catalytic cracking, hydrocracking, isomerization, oligomerization, the conversion of alcohols or ethers, and the alkylation of aromatics. In particular, the use of SAPOs in converting alcohols or ethers to olefin products, particularly ethylene and propylene, is becoming of greater interest for large scale, commercial production facilities.

As is known in the development of new large scale, commercial production facilities in the commodity chemical business, many problems arise in the scale up from laboratory and pilot plant operations. Scale up problems arise in catalytic reaction systems where large scale operation will be several orders of magnitude larger than typical pilot scale facilities. For example, conventional laboratory scale processes of making olefin products from oxygenate feed are conducted with catalyst loads of about 5 grams. Conventional large pilot plant operations may utilize as much as 50 kg of catalyst, making on the order of 20 kg/hr ethylene and propylene product, but this is nevertheless minuscule in comparison to what a large scale, commercial production facility would produce, if one were in existence today. Large scale, commercial production facilities, can require a catalyst loading of anywhere from 1,000 kg to 700,000 kg, producing anywhere from 600 to 400,000 kg/hr of ethylene and propylene product.

Operating large scale, commercial production facilities clearly presents great challenges in the development of the catalyst production-to-use chain. The term "production-to-use chain" refers to the entire area of activities beginning with the production of molecular sieve, including such activities as receipt of starting materials, on through the crystallization process. Also included in the production-to-use chain are intermediate activities which include formulation of the sieve with binders and other materials, activation of the manufactured sieve and finished catalyst; storage, transport, loading, unloading of molecular sieve and finished catalyst; as well as other practices associated with the handling and preparation of the sieve and finished catalyst for its ultimate use. The production-to-use chain ends at the point when the molecular sieve is introduced into the reaction system. For purposes of this invention, the end of the production-to-use chain does not necessarily mean the instant when the molecular sieve is introduced into the reaction system, since large scale systems are very large and instantaneous measurements are not practically feasible. In large scale systems, the production-to-use chain may be considered as completed some time within 12 hours of loading catalyst into the reaction system.

Since information to date relating to production of olefin products by catalytic conversion of oxygenate feedstock has been limited to laboratory and small pilot plant activities, little if any attention has been paid to the problems associated with the intermediate activities in the production-to-use chain. For example, little attention has been focused on the impact of storage, transport, etc. on catalyst activity, since small scale activity is rather easily manageable. While today only relatively small quantities of catalyst are stored and transported, large quantities of materials will need to be handled for commercial operations. Commercial operations may be required to store large quantities of sieve and catalyst materials for considerable periods of time, at multiple locations, and under rather rigorous industrial conditions.

As the management of sieve and catalyst in the catalyst production-to-use chain expands in volume and complexity, a likelihood exists that millions of dollars will be tied up in catalyst inventory, and the value of the sieve and catalyst will be lost if quality is not maintained at every step. Loss of quality will necessarily translate to loss of product quality, as well as loss of product quantity, and these product losses could far outweigh the cost of the sieve and catalyst.

Although some work has been published relating to the intermediate activities in the catalyst production-to-use chain, few of the problems associated therewith have been addressed. For example, U.S. Pat. No. 4,681,864 to Edwards et. al. discuss the use of SAPO-37 molecular sieve as a commercial cracking catalyst. It is disclosed that activated SAPO-37 molecular sieve has poor stability, and that stability can be improved by using a particular activation process. In this process, organic template is removed from the core structure of the sieve just prior to contacting with feed to be cracked. The process calls for subjecting the sieve to a temperature of 400–800° C. within the catalytic cracking unit.

U.S. Pat. No. 5,185,310 to Degnan et al. discloses another method of activating silicoaluminophosphate molecular sieve compositions. The method calls for contacting a crystalline silicoaluminophosphate with gel alumina and water, and thereafter heating the mixture to at least 425° C. The heating process is first carried out in the presence of an oxygen depleted gas, and then in the presence of an oxidizing gas. The object of the heating process is to enhance the acid activity of the catalyst. The acid activity is enhanced as a result of the intimate contact between the alumina and the sieve.

Briend et al., *J. Phys. Chem.* 1995, 99, 8270–8276, teach that SAPO-34 loses its crystallinity when the template has been removed from the sieve and the de-templated, activated sieve has been exposed to air. Data are presented, however, which suggest that over at least the short term, this crystallinity loss is reversible. Even over a period of perhaps two years, the data suggest that crystallinity loss is reversible when certain templates are used.

EP-A2-0 203 005 also discusses the use of SAPO-37 molecular sieve in a zeolite catalyst composite as a commercial cracking catalyst. According to the document, if the organic template is retained in the SAPO-37 molecular sieve until a catalyst composite containing zeolite and the SAPO-37 molecular sieve is activated during use, and if thereafter the catalyst is maintained under conditions wherein exposure to moisture is minimized, the crystalline structure of the SAPO-37 zeolite composite remains stable.

A group of researchers at ExxonMobil Chemical Company has recently discovered that activated SAPO molecular sieve will exhibit a loss of catalytic activity when exposed to a moisture-containing environment. This loss of activity can occur between the time the catalyst is activated and even after as little as one day of storage. Although ways have been found to inhibit loss of catalytic activity, it would be highly beneficial to find a way to reverse the decrease of catalytic activity in a molecular sieve exposed to a moisture-containing environment.

SUMMARY OF THE INVENTION

In order to overcome the various problems associated with decrease of activity of a molecular sieve due to contact by moisture, this invention provides a way to reverse such decrease, i.e., to rejuvenate the molecular sieve. In general, this invention provides a process for rejuvenating a molecular sieve which comprises providing a molecular sieve having a methanol uptake index of less than 1; and contacting the molecular sieve with anhydrous liquid or vapor until the methanol uptake ratio is increased by at least 10%.

Preferably, the molecular sieve is a silicoaluminophosphate molecular sieve and it is provided having a methanol uptake index of less than 0.5, more preferably a methanol uptake index of less than 0.3, and most preferably, a methanol uptake index of less than 0.15. In another preferred embodiment, the methanol uptake ratio is increased by at least 50%, more preferably by at least 100%, and most preferably by at least 500%.

It is also desirable that the molecular sieve be contacted with anhydrous liquid or vapor until a methanol uptake ratio of at least 0.4 is achieved, preferably at least 0.6, more preferably at least 0.7, and most preferably at least 0.8.

In another preferred embodiment of the invention, the anhydrous liquid or vapor is polar. Desirably, the anhydrous liquid or vapor contains not greater than about 30 wt. % water, preferably not greater than about 20 wt. % water, and more preferably not greater than about 10 wt. % water. It is also desirable that the anhydrous liquid or vapor have a kinetic diameter of not greater than 1.5 times the average pore size of the molecular sieve, preferably not greater than 1.3 times the average pore size. It is further desirable that the anhydrous liquid or vapor have a gas-phase proton affinity greater than or equal to the proton affinity of water.

Desirably, the anhydrous liquid or vapor is an alcohol, ether, ketone, carboxylic acid, aldehyde, nitrogen containing organic bases or mixtures thereof. Preferably, the anhydrous liquid or vapor is selected from the group consisting of methanol, ethanol, dimethyl ether, propylamine, and acetonitrile. More preferably, the anhydrous liquid or vapor is methanol.

The silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferably, the silicoaluminophosphate is selected from the group consisting of SAPO-18, SAPO-34, SAPO-35, SAPO-44, SAPO-47, the metal containing forms thereof, and mixtures thereof. More preferably, the silicoaluminophosphate is selected from the group consisting of SAPO-18 and SAPO-34, the metal containing forms thereof, and mixtures thereof.

In an alternative embodiment, the invention includes a method of making an olefin product from an oxygenate-containing feedstock. The method comprises forming a rejuvenated molecular sieve; and contacting the rejuvenated molecular sieve with an oxygenate-containing feedstock to produce an olefin product.

Desirably, the oxygenate-containing feedstock is selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferably, the oxygenate-containing feedstock is selected from the group consisting of methanol, dimethyl ether, and mixtures thereof.

It is also desirable that, in the method of making the olefin product, the rejuvenated molecular sieve is contacted with the oxygenate-containing feedstock at a temperature of 200° C. to 700° C. Preferably the rejuvenated molecular sieve is contacted with the oxygenate-containing feedstock at a WHSV of at least 20 hr$^{-1}$. It is also preferred that the silicoaluminophosphate molecular sieve is provided in catalyst form, i.e., with a binder material.

The invention also provides contacting the olefin product a polyolefin-forming catalyst under conditions effective to form a polyolefin. The preferred olefin product contains ethylene and/or propylene, which can be used to form polyethylene and/or polypropylene. The olefin and polyolefin products so formed are also considered to be encompassed by the invention.

BRIEF DESCRIPTION OF THE DRAWINGS

The invention will be better understood by reference to the Detailed Description of the Invention when taken together with the attached drawings, wherein.

DETAILED DESCRIPTION OF THE INVENTION

SAPO molecular sieve catalysts, in particular, are susceptible to structural changes as a result of continued exposure to even low levels of moisture. Such authorities as Paulitz et al., *Microporous Materials*, 2, 223–228 (1994), however, have shown through X-ray diffraction (XRD), nuclear magnetic resonance (NMR), infrared (IR) and nitrogen ($N_2$) adsorption analyses that the structural change is largely reversible. These X-ray diffraction studies have been found to be unreliable in determining loss of catalytic activity. For example, Pualitz et al. have shown that SAPO molecular sieve once structurally altered by contact with moisture can be rejuvenated by calcination to exhibit its typical X-ray diffraction pattern. However, the same procedure has been shown not to rejuvenate catalytic activity of the molecular sieve. See, for example, U.S. Ser. No. 09/391,770 to ExxonMobil Chemical Company.

The loss of catalytic activity as a result of contact of molecular sieve with moisture presents a problem in the commercial production-to-use chain where storage and transport of molecular sieve and catalyst can occupy relatively long periods of time. For example, it is possible that molecular sieve or catalyst containing molecular sieve can be stored anywhere from 12 hours to many months, perhaps as long as one year before its use in a catalytic process. This stored sieve or catalyst is likely not to have a template within its internal pore structure as a result of having been removed by calcination prior to storage. Such a sieve or catalyst would be especially susceptible to damage by contact with moisture. Even partial loss of catalytic activity is of particular concern in a large scale catalytic process. As defined herein, a large scale catalytic process is one having a reactor loading in excess of 50 kg, particularly one having a reactor system loading in excess of 500 kg, especially one having a reactor loading in excess of 5000 kg.

SAPO molecular sieve, as well as catalyst containing SAPO molecular sieve, which exhibits decreased catalytic activity as a result of contact with moisture can be rejuvenated by contacting the sieve or catalyst with anhydrous liquid or vapor. According to this invention, rejuvenated molecular sieve is determined using a methanol uptake ratio. A molecular sieve having a methanol uptake ratio of less than 1 is capable of being rejuvenated.

As used herein, methanol uptake ratio is defined as the methanol adsorption capacity (wt. %) of a microporous SAPO molecular sieve having been rejuvenated by contact with an anhydrous liquid or vapor, divided by the maximum methanol adsorption capacity (wt. %) of a SAPO molecular sieve (i.e., the initial methanol adsorption capacity). The anhydrous liquid or vapor preferably has a kinetic diameter of not greater than about 1.5 times the opening (i.e., average pore size) of SAPO molecular sieve, preferably not greater than about 1.3 times. The term kinetic diameter as used herein means the average, effective size as measured in an uptake experiment.

As used herein, anhydrous liquid or vapor refers to a chemical composition, either in the liquid or vapor state. Preferably anhydrous liquid or vapor contains no more than about 30 wt. % water, preferably no more than about 20 wt. % water, more preferably no more than about 10 wt. % water.

It is further desirable in this invention that the anhydrous liquid or vapor have a gas-phase proton affinity greater than or equal to the proton affinity of water. The gas phase proton affinity will desirably be greater than or equal to 166.5 kcal/mol. Values of gas phase proton affinities can be found in Azulejko, J. E. and McMahon, T. B., *JACS,* 115,7839 (1993) and references cited therein, the descriptions of which are incorporated herein by reference.

Preferably, the anhydrous liquid or vapor is an alcohol, ether, ketone, carboxylic acid, aldehyde, nitrogen containing organic bases or mixtures thereof. Particularly desirable compounds are alcohols, especially $C_1$–$C_{12}$ alcohols, and particularly methanol and linear alcohols; ethers, especially dimethyl ether and other linear alkyl ethers; ketones, especially acetone; amines, especially ethylanime and propylamine; and acetonitrile. Other suitable compounds include aromatics, especially benzene, toluene and other methylated aromatics, and mixtures thereof; olefins, particularly linear olefins, most desirably propylene and butylenes, and mixtures thereof; and multiple bond compounds such as acetylene, methyl acetylene, and butadiene. Another suitable compound includes carbon dioxide.

In this invention, a molecular sieve is considered to be rejuvenated when a methanol uptake ratio of at least 0.4 is achieved, preferably when a methanol uptake ratio of at least 0.6 is achieved, more preferably when a methanol uptake ratio of at least 0.7 is achieved, and most preferably when a methanol uptake ratio of at least 0.8 is achieved. Thus, in the more practical form of this invention, a molecular sieve having a methanol uptake index of less than about 0.4 is a more likely candidate for rejuvenation, although a molecular sieve having a methanol uptake index of less than 1 is capable of being rejuvenated.

In this invention, rejuvenation is considered to be demonstrated when the rejuvenation process results in a relative increase in the methanol uptake index of at least about a 10%. Preferably, the rejuvenation process will result in an increase in the methanol uptake index of at least about 50%, more preferably at least about 100%, and most preferably at least about 500%, the increase being calculated as the change before rejuvenation and after rejuvenation on a percent basis.

The lower the methanol uptake index of a molecular sieve, the more suitable the molecular sieve for rejuvenation. From an efficiency standpoint, it is preferable to rejuvenate a molecular sieve which has a methanol uptake index of less than about 0.3, more preferably less than about 0.2, and most preferably less than about 0.15. Complete rejuvenation results in a methanol uptake index of 1.

To calculate methanol uptake index, methanol adsorption capacity must be measured. Techniques for measuring methanol adsorption capacity are known to those of ordinary skill in the art. In a preferred technique, about 5 mg of sample is introduced into a thermogravimetric analyzer (TGA). The sample is subjected to a heat treatment process, which includes: (1) heating from room temperature to 450° C., with a heat up rate of 20° C./min. in air; (2) holding at 450° C. for 40 min. in air; and cooling to 30° C. in air. After the sample has reached 30° C., the air flow in the TGA is switched to a methanol containing nitrogen flow with a methanol partial pressure of 0.09 atm. The sample is contacted with this nitrogen/methanol mixture for 180 minutes. The methanol adsorption capacity is the weight percent weight increase after the 180 minutes contact with the methanol vapor.

In general the anhydrous liquid or vapor is contacted with the molecular sieve to be rejuvenated in a batch or continuous process. In either process, the liquid or vapor is contacted with the molecular sieve for a time which can range from several minutes to hours or up to several weeks. Contact can be stopped at the time a desired degree of rejuvenation has been obtained. Desirably contacting continues until a relative increase in the methanol uptake index of at least about a 10% has been obtained. Desirably, the vapor or liquid is flowed over the molecular sieve at temperature in the range of from about 0 to 100° C., preferably from about 10 to 60° C.

The pressure at which contact between liquid or vapor and molecular sieve is made is not critical. Desirably, pressure is in the range of from vacuum conditions to about 100 psia, preferably from about 0 to 50 psia.

The catalyst that is used in this invention is one that incorporates a silicoaluminophosphate (SAPO) molecular sieve. The molecular sieve comprises a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, *J. Phys. Chem.,* 92, 3965 (1988). The desired SAPO molecular sieves will exhibit one or more peaks in the $^{29}Si$ MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A Si/Al$_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

In general, silicoaluminophosphate molecular sieves comprise a molecular framework of corner-sharing [SiO$_2$], [AlO$_2$], and [PO$_2$] tetrahedral units. This type of framework is effective in converting various oxygenates into olefin products.

The [PO$_2$] tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The [AlO$_2$] tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [SiO$_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the $Atlas\ of\ Zeolite\ Structural\ Types$, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about $20\mu$ to $3,000\mu$ more preferably about $30\mu$ to $200\mu$, most preferably about $50\mu$ to $150\mu$.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

It is particularly desirable that the rejuvenated molecular sieve of this invention be used in the process of making olefin product from an oxygenate-containing feedstock. In one embodiment of this invention, a feed containing an oxygenate, and optionally a diluent or a hydrocarbon added separately or mixed with the oxygenate, is contacted with a catalyst containing a rejuvenated SAPO molecular sieve in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to, helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary. To account for this variation, the "average catalyst feedstock exposure index (ACFE index)" is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor. The measurement should be made over an equivalent time interval, and the time interval should be long enough to smooth out fluctuations in catalyst or feedstock rates according to the reactor and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques," *Circulating Fluidized Beds*, Grace, Avidan, & Knowlton, eds., Blackie, 1997 (336–337), the descriptions of which are expressly incorporated herein by reference.

In this invention, only the molecular sieve in the catalyst sent to the reactor may be used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been regenerated or does not contain fresh catalyst, is not to be used in the determination of ACFE index.

In a preferred embodiment of this invention, a feed containing an oxygenate, and optionally a hydrocarbon, either separately or mixed with the oxygenate, is contacted with a catalyst containing a rejuvenated SAPO molecular sieve at process conditions effective to produce olefins in a reactor where the catalyst has an ACFE index of at least about 1.0, preferably at least 1.5. An ACFE index in the range of about 1.0 to 20 is effective, with a range of about 1.5–15 being desirable. A range of about 2–12 is particularly preferred.

Any standard reactor system can be used, including fixed bed, fluid bed or moving bed systems. Preferred reactors are co-current riser reactors and short contact time, countercurrent free-fall reactors in which an oxygenate feedstock can be contacted with a molecular sieve catalyst at a WHSV of at least about 20 $hr^{-1}$, preferably in the range of from about 20 $hr^{-1}$ to 1000 $hr^{-1}$, and most preferably in the range of from about 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the rejuvenated catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to 700° C., preferably from about 300° C. to 600° C., more preferably from about 350° C. to 550° C. At the lower end of the temperature range, the formation of the desired olefin products may become markedly slow. At the upper end of the temperature range, the process may not form an optimum amount of product.

It is highly desirable to operate at a temperature of at least 300° C. and a Temperature Corrected Normalized Methane Sensitivity (TCNMS) of less than about 0.016. It is particularly preferred that the reaction conditions for making olefin from oxygenate comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

The conversion of oxygenates to produce light olefins may be carried out in a variety of catalytic reactors. Reactor types include fixed bed reactors, fluid bed reactors, and concurrent riser reactors as described in "Free Fall Reactor," *Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", *Fluidization and Fluid-Particle Systems*, pages 48–59, F. A. Zenz and D. F. Othmo, Reinhold Publishing Corp., N.Y. 1960, the detailed descriptions of which are also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10–200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

Figure 1:
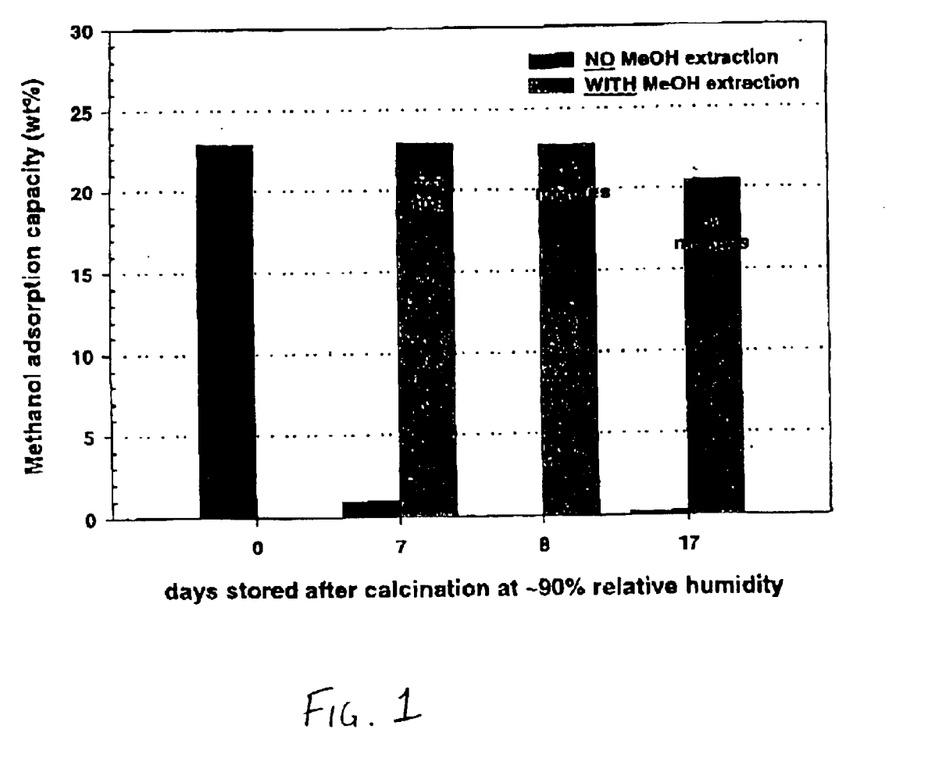
FIG. 1 shows rejuvenation of SAPO molecular sieve following contact with methanol.

A SAPO-34 molecular sieve synthesized with a morpholine template was calcined under $N_2$ for 5 hours, followed by air for 3 hours, at a temperature of 650° C. to remove the template. Samples of the detemplated SAPO-34 was stored at room temperature at a relative humidity of ~90% (saturated $KNO_3$ solution) for 7, 8 and 17, days, respectively. The methanol adsorption capacity of the stored samples, as well as a fresh sample (0 days stored) were determined before and after contacting with dry methanol (dried with 3A molecular sieve). The methanol adsorption capacities were measured in a conventional thermographic analyzer (TGA). In a typical experiment, a sample was heated in air from room temperature to 200° C. at 20° C./min, held for 30 minutes at 200° C., and then ramped at a rate of 20° C./min to 625° C., and held for 30 minutes. The sample was then cooled to room temperature and the methanol adsorption analyzed. The results are shown in FIG. 1. From FIG. 1, it can be seen that the methanol adsorption capacity can be largely rejuvenated to that of fresh molecular sieve by contacting with methanol. Even after a 17 day storage at relatively high humidity, the methanol uptake ratio was calculated to be ~0.87.

EXAMPLE 2

Figure 2:
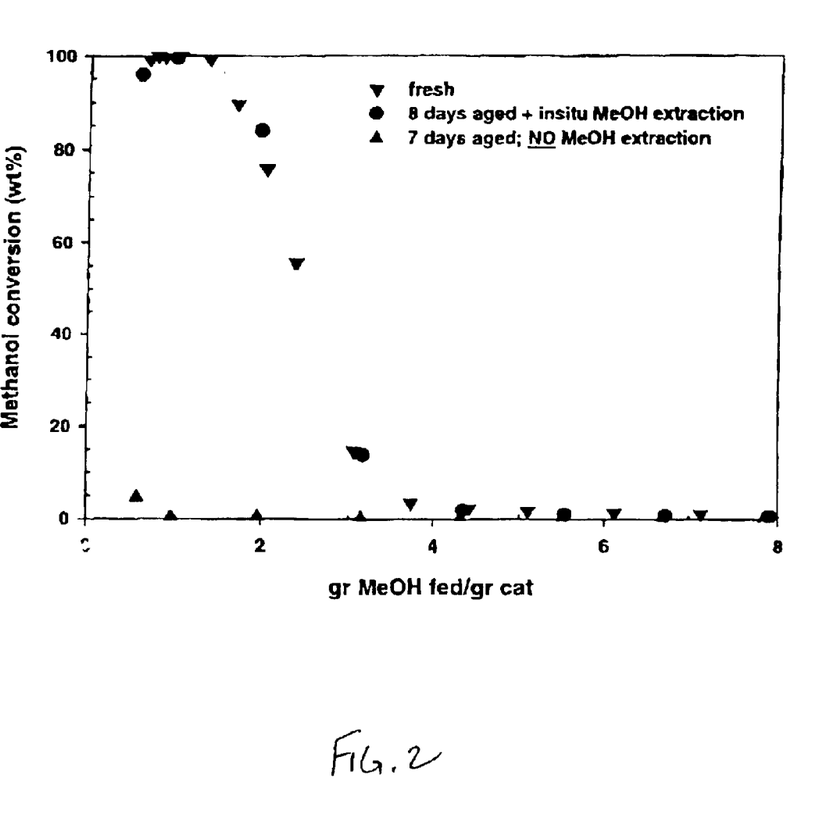
FIG. 2 shows methanol conversion for fresh, rejuvenated, and moisture aged SAPO molecular sieve.

A sample of SAPO-34 molecular sieve was heated in situ (i.e., in a fixed bed, continuous reactor) under nitrogen at 650° C. for 1 hour to remove the morpholine template. After template removal, methanol was continuously fed to the reactor at a WHSV of 25 $hr^{-1}$ while maintaining the reaction temperature at 450° C. and the reactor pressure at 25 psig. Reaction products were analyzed with an on-line GC equipped with a FID and TCD detector. Methanol conversion was calculated as: 100−(wt % methanol+dimethyl ether) left in product. Methanol conversion as a function of the amount of methanol fed/gram of molecular sieve in the reactor is shown in FIG. 2, with the label "fresh."

EXAMPLE 3

A sample of SAPO-34 molecular sieve was heated ex situ under nitrogen for 5 hours at 650° C., followed by heating in air for 3 hours, to remove the morpholine template. The detemplated sieve was then stored under ambient conditions for 7 days. After the 7 day storage, the sample was heated in situ (i.e., in a fixed bed, continuous reactor) under nitrogen at 625° C. for 1 hour. The sample was then evaluated for methanol conversion as in Example 1. The result is shown in FIG. 2, with the label "7 days aged; NO MeOH extraction."

EXAMPLE 4

A sample of SAPO-34 molecular sieve was heated ex situ under nitrogen for 5 hours at 650° C., followed by heating in air for 3 hours at 650° C. to remove the morpholine template. The detemplated sieve was then stored under ambient conditions for 8 days. After the 8 day storage, the sample was contacted with methanol in situ (i.e., in a fixed bed, continuous reactor) by pumping methanol (~7.5 gr/hr) over the molecular sieve at room temperature for 1.5 hours. After contact, the molecular sieve was contacted with nitrogen (100 ml/min) at room temperature for 80 minutes to evaporate the methanol. The sieve was then heated under nitrogen at 625° C. for 1 hour. The sample was then evaluated for methanol conversion as in Example 1. The result is shown in FIG. 2, with the label "8 days aged+in situ MeOH extraction."

FIG. 2 shows that a SAPO molecular sieve aged for 7 days has almost no catalytic activity. However, a SAPO molecular sieve aged for 8 days and contacted with methanol will rejuvenate the catalytic activity of the molecular sieve to essentially that of a fresh or non-aged molecular sieve.

EXAMPLE 5

A SAPO-34 molecular sieve was heated under nitrogen for 5 hours, followed by heating in air for 3 hours at a temperature of 650° C. to remove the template. Samples of the detemplated SAPO-34 were stored at room temperature at a relative humidity of ~90% (saturated KNO3 solution) sufficiently long to obtain a methanol uptake ratio equal to or less than 0.3. The samples were then contacted with a polar liquid or vapor, and the methanol uptake ratio was determined. The results are shown in Table 1.

TABLE 1

| Extracting Liquid or Vapor | Methanol Uptake Ratio Before Extraction | Methanol Uptake Ratio After Extraction |
| --- | --- | --- |
| methanol | 0.09 | 1 |
| 9 wt % water in methanol | 0.3 | 0.9 |
| 16 wt % water in methanol | 0.2 | 0.9 |
| 20 wt % water in methanol | 0.09 | 0.4 |
| 27 wt % water in methanol | 0.2 | 0.5 |
| methanol vapor; methanol partial pressure ~ 0.12 bar | 0.09 | 0.9 |
| ethanol | 0.2 | 0.85 |
| propylamine | 0.09 | 0.9 |
| acetonitrile | 0.09 | 0.9 |

The methanol uptake ratio is a measurement of the degree of rejuvenation. The percent increase of the methanol uptake ratio is a direct indication of the percent increase in catalyst rejuvenation. Table 1 shows that polar compounds are particularly effective in rejuvenating the catalytic activity of a SAPO molecular sieve.

Having now fully described this invention, it will be appreciated by those skilled in the art that the invention can be performed within a wide range of parameters within what is claimed, without departing from the spirit and scope of the invention.

What is claimed is:

1. A method of making an olefin product from an oxygenate-containing feedstock, comprising
   providing a silicoaluminophosphate molecular sieve having decreased catalytic activity as a result of contact with moisture; and
   contacting the molecular sieve with anhydrous liquid or vapor until the molecular sieve has a methanol uptake ratio that is increased by at least 10% compared to the provided molecular sieve, thereby forming a rejuvenated molecular sieve; and
   contacting the rejuvenated molecular sieve with an oxygenate-containing feedstock to produce an olefin product.

2. The method of claim 1, wherein the methanol uptake ratio is increased by at least 50%.

3. The method of claim 2, wherein the methanol uptake ratio is increased by at least 100%.

4. The method of claim 3, wherein the methanol uptake ratio is increased by at least 500%.

5. The method of claim 1, wherein the anhydrous liquid or vapor contains less than 30 wt. % water.

6. The method of claim 5, wherein the anhydrous liquid or vapor contains less than 20 wt. % water.

7. The method of claim 6, wherein the anhydrous liquid or vapor contains less than 10 wt. % water.

8. The method of claim 1, wherein the anhydrous liquid or vapor has a kinetic diameter of not greater than 1.5 times the average pore size of the molecular sieve.

9. The method of claim 8, wherein the anhydrous liquid or vapor has a kinetic diameter of not greater than 1.3 times the average pore size of the molecular sieve.

10. The method of claim 1, wherein in the anhydrous liquid or vapor is an alcohol, ether, ketone, carboxylic acid, aldehyde, nitrogen containing organic base, or a mixture thereof.

11. The method of claim 1, wherein the anhydrous liquid or vapor is selected from the group consisting of methanol, ethenol dimethyl ether, acetone, propylaniine, and acetonitrile.

12. The method of claim 11, wherein the anhydrous liquid or vapor is methanol.

13. The method of claim 1, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

14. The method of claim 13, wherein the silicoaluminophosphate molecular sieve is selected from the group consisting of SAPO-18, SAPO-34, SAPO-35, SAPO-44, SAPO-47, the metal containing forms thereof, and mixtures thereof.

15. The method of claim 14, wherein the silicoaluminophosphate molecular sieve is selected from the group consisting of SAPO-18, SAPO-34, the metal containing forms thereof, and mixtures thereof.

16. The method of claim 1, wherein the oxygenate-containing feedstock is selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

17. The method of claim 16, wherein the oxygenate-containing feedstock is selected from the group consisting of methanol, dimethyl ether, and mixtures thereof.

18. The method of claim 1, wherein the rejuvenated molecular sieve is contacted with the oxygenate-containing feedstock at a temperature of 200° C. to 700° C.

19. The method of claim 1, wherein the rejuvenated molecular sieve is contacted with the oxygenate-containing feedstock at a WHSV of at least 20 hr$^{-1}$.

20. The method of claim 1, wherein the silicoaluminophosphate molecular sieve is provided with a binder material.

21. The method of claim 20, wherein the olefin product is contacted with a polyolefin-forming catalyst under conditions effective to form a polyolefin.

22. The method of claim 1, wherein the anhydrous liquid or vapor has a gas-phase proton affinity greater than or equal to the proton affinity of water.

* * * * *